US00PP16285P3

(12) United States Plant Patent

Kanaya et al.

(10) Patent No.: US PP16,285 P3
(45) Date of Patent: Feb. 21, 2006

(54) *CALIBRACHOA* PLANT NAMED 'SUNBEL-LABU'

(50) Latin Name: ***Calibrachoa* sp.**
Varietal Denomination: Sunbel-labu

(75) Inventors: Takeshi Kanaya, Omihachiman (JP); Yasuyuki Murakami, Gamo-gun (JP)

(73) Assignee: Suntory Flowers Limited, Tokyo (JP)

( * ) Notice: Subject to any disclaimer, the term of this patent is extended or adjusted under 35 U.S.C. 154(b) by 9 days.

(21) Appl. No.: 10/812,859

(22) Filed: Mar. 29, 2004

(65) Prior Publication Data

US 2005/0216989 P1 Sep. 29, 2005

(51) Int. Cl.
*A01H 5/00* (2006.01)

(52) U.S. Cl. ..... Plt./263
(58) Field of Classification Search ..... Plt./263, Plt./356
See application file for complete search history.

(56) References Cited

U.S. PATENT DOCUMENTS

| | | | | |
|---|---|---|---|---|
| PP6,914 P | | 7/1989 | Tsuda et al. | |
| PP9,557 P | | 5/1996 | Suzuki et al. | |
| PP9,754 P | | 12/1996 | Suzuki et al. | |
| PP10,279 P | | 3/1998 | Murakami | |
| PP10,355 P | | 4/1998 | Murakami | |
| PP10,904 P | | 5/1999 | Hansson | |
| PP11,558 P | | 10/2000 | Murakami | |
| PP14,125 P2 | | 9/2003 | Miyazaki | |
| PP15,345 P2 | * | 11/2004 | Westhoff | Plt./263 |

FOREIGN PATENT DOCUMENTS

| | | |
|---|---|---|
| JP | PBR 2707 | 6/1991 |
| JP | PBR 7390 | 9/1999 |
| JP | PBR 13924 | 10/2001 |

OTHER PUBLICATIONS

UPOV ROM GTITM Computer Database, GTI Jouve Retrieval Software 2004/06 Citations for 'Sunbel–labu'.*

COPF Newsletter vol. 16 #2—Jul. 2004 p. 3—available at: http:www.cof.org/auwa/pdf/News_July_2004.pdf.*

Reis, Claudia dos, Sajo, Maria das Gracas and Stehmann, Joao Renato. Leaf Structure and Taxonomy of Petunia and *Calibrachoa* (Solanaceae). Braz. arch. biol. technol., Mar. 2002, vol. 45, No. 1, pp. 59–66.*

Flower & Green, the newest Catalog 2004, Suntory Flowers, Ltd., (4 pp), Published 2003, with brief English explanation and partial translation of p. 4.

Suntory Collection 2004, Moerheim New Plant bv, (6 pp), Published 2003 with brief English explanation.

Colour Wave Collection 2003–04, Ramm Botanicals Pty. Ltd., (3 pp), Published 2002 with brief English translation.

Explanation of Publication of Japanese PBR Registrations and family documents therein.

* cited by examiner

*Primary Examiner*—Kent Bell
*Assistant Examiner*—W. C. Haas
(74) *Attorney, Agent, or Firm*—Christie, Parker and Hale, LLP

(57) ABSTRACT

Disclosed herein is a new and distinct variety of *Calibrachoa* plant having a spreading growth habit. The *Calibrachoa* plant has abundant branching, and a great profusion of blooms, the whole plant remaining in bloom for a considerable period of time. The flowers are single and very small, the petals having light purple color with deep reddish purple midvein. The bottom color of the corolla throat is vivid yellow and the outside of the coroll tube is dark pink. The plant exhibits high resistance to heat, cold, rain and disease.

2 Drawing Sheets

Botanical designation: *Calibrachoa* sp.
Variety denomination: 'Sunbel-labu'.

BACKGROUND OF THE VARIETY

The present invention relates to a new variety of *Calibrachoa* plant, which originated from the crossing of a *Calibrachoa* hybrid variety, botanically known as *Calibrachoa* sp., with '9LB6' as the female parent and '9LB1' as the male parent.

The female parent '9LB6' (unpatented) used in the crossing to produce 'Sunbel-labu' is a strain of our breeding lines having light purple flowers (near R.H.S. N82B). The flower of '9LB6' is smaller than that of 'Sunbel-labu'.

The male parent '9LB1' (unpatented) used in the crossing to produce 'Sunbel-labu' is a strain of our breeding lines, having light purple flowers (near R.H.S. N81C). The plant height of '9LB1' is higher than that of 'Sunbel-labu'.

In April 2000, crossing of '9LB6' as the female parent and '9LB1' as the male parent was conducted at Yokaichi-shi, Shiga-ken, Japan. In September 2000, fifty seedlings were obtained from the crossing. These seedlings were grown in pots in glasshouses and were evaluated. One seedling was selected in view of its growth habit, flower size and color in Septemeber 2001. That seedling was propagated by cutting and a trial was carried out by flower potting and bedding from April to October 2002. The botanical characteristics of that plant were then examined, using similar varieties 'Sunbelchipi' (U.S. Plant Pat. No. 10,355) and 'Sunbelkubu' (U.S. Plant Pat. No. 10,279 ) for comparison. As a result, it was concluded that this *Calibrachoa* plant is distinguishable from any other variety, whose existence is known to us, and is uniform and stable in its characteristics. The new variety of *Calibrachoa* plant was named 'Sunbel-labu'.

In the following description, the color-coding is in accordance with The Horticultural Colour Chart of The Royal Horticultural Society, London, England (R.H.S.).

SUMMARY OF THE VARIETY

This new variety is unlike any commercially avaliable *Calibrachoa* known to the inventors as evidenced by the following unique combinations of characteristics.

1. Spreading growth habit with abundant branching.
2. A great profusion of blooms, with the entire plant remaining in bloom for a considerable period of time.
3. The flowers are single and very small. The petal color is light purple (near R.H.S. 76A) with deep reddish purple (near R.H.S.77A) midvein.
4. The plant has a high resistance to rain, cold, heat and diseases.

The new variety 'Sunbel-labu' differs from the similar variety 'Sunbelchipi' in the following points.

1. The leaf of 'Sunbel-labu' is smaller than that of 'Sunbelchipi'.
2. The petal color of 'Sunbel-labu' is light purple (near R.H.S. 76A) with deep reddish purple (R.H.S.77A) midvein, while that of 'Sunbelchipi' is vivid purplish red (near R.H.S.N57A).
3. The bottom color of the corolla throat of 'Sunbel-labu' is vivid yellow (near R.H.S.14B) , while that of 'Sunbelchipi' is strong yellow (near R.H.S.9A).
4. The outside color of the corolla tube of 'Sunbel-labu' is dark pink (near R.H.S. 182C), while that of 'Sunbelchipi' is brilliant yellow (near R.H.S. 5C).
5. The apex shape of petal of 'Sunbel-labu' is rounded, while that of 'Sunbelchipi' is obtuse.

The new variety 'Sunbel-labu' differs from the similar variety 'Sunbelkubu' in the following points.

1. The growth habit of 'Sunbel-labu' is spreading, while that of 'Sunbelkubu' is decumbent.
2. The leaf length of 'Sunbel-labu' is shorter than that of 'Sunbelkubu'.
3. The petal color of 'Sunbel-labu' is light purple (near R.H.S. 76A) with deep reddish purple (near R.H.S.77A) midvein, while that of 'Sunbelkubu' is vivid purple (near R.H.S.N81A).
4. The bottom color of the corolla throat of 'Sunbel-labu' is vivid yellow (near R.H.S.14B, while that of 'Sunbelkubu' is brilliant yellow (near R.H.S.5C).
5. The outside color of the corolla tube 'Sunbel-labu' is dark pink (near R.H.S.182C), while that of 'Sunbelkubu' is pale yellow green (near R.H.S.1D).
6. The apex shape of the petal of 'Sunbel-labu' is rounded, while that of 'Sunbelkubu' is obtuse.

This new variety of *Calibrachoa* plant 'Sunbel-labu' was asexually reproduced by the use of cuttings in Yokaichi-shi, Shiga-ken, Japan, and homogeneity and stability were comfirmed. The instant plant retains its distinctive characteristics and reproduces true to type in successive generations.

BRIEF DESCRIPTION OF THE PHOTOGRAPHS

The depicted plants had been reproduced by the use of cuttings and were photographed during September 2002 while growing outdoors in 24 cm pots at an age of approximately 8 months at Yokaichi-shi, Shiga-ken, Japan.

DESCRIPTION OF THE VARIETY

Figure 1:
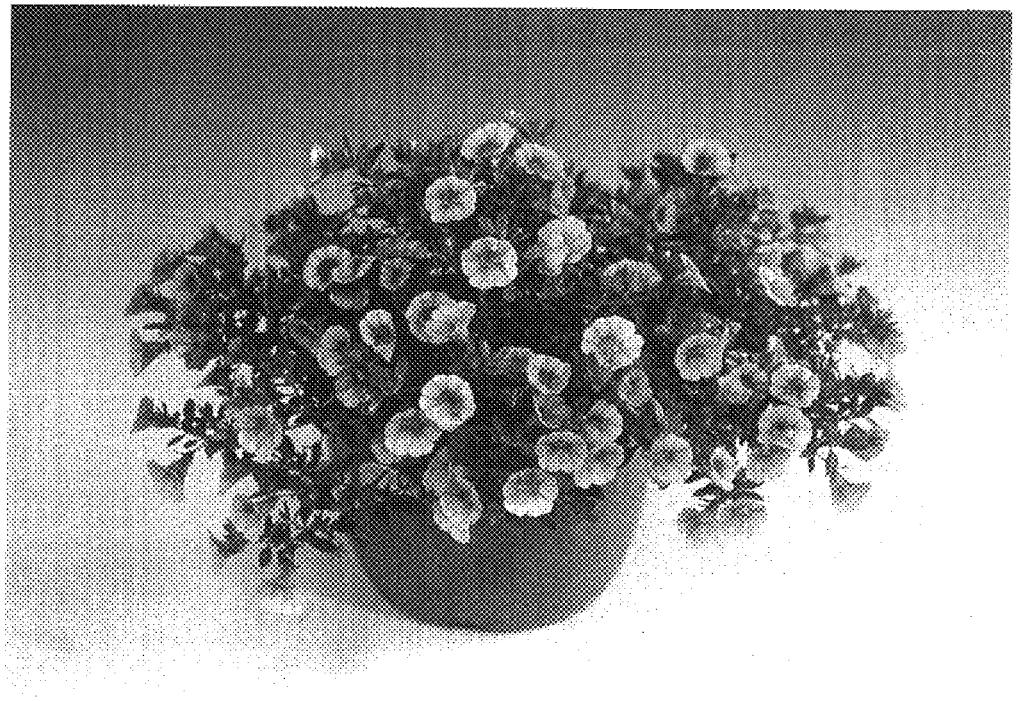
FIG. 1 is a photograph of a typical plant of the new variety of *Calibrachoa* plant 'Sunbel-labu' while growing in a pot.
Figure 2:
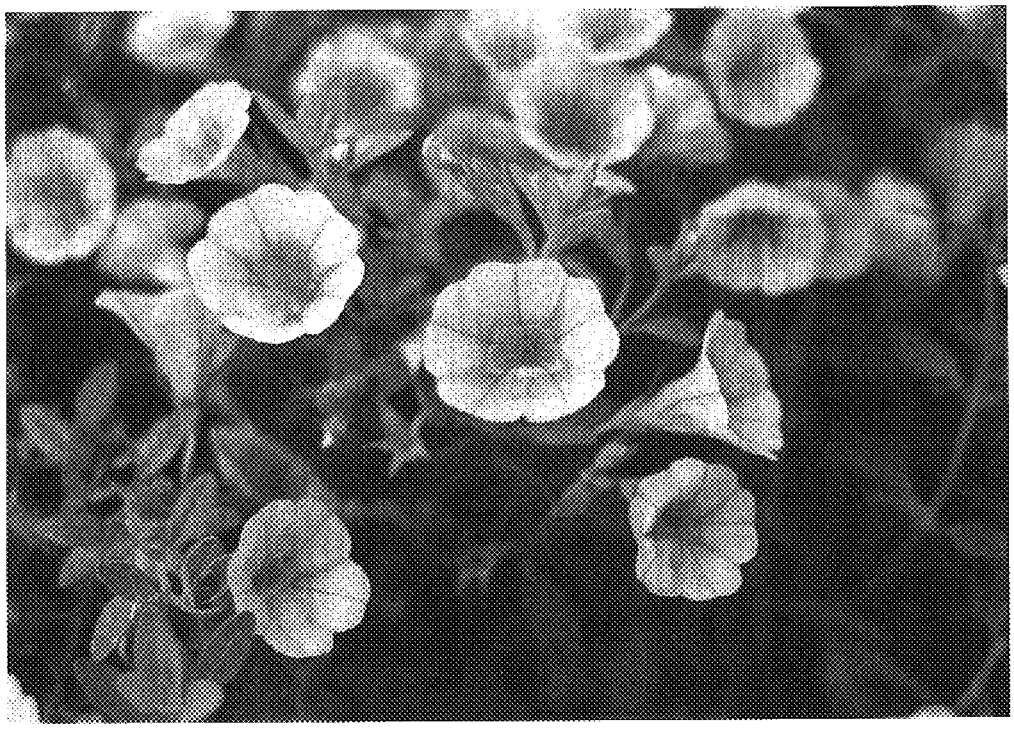
FIG. 2 is a photograph of a close view of flowers and leaves of the new variety of *Calibrachoa* plant 'Sunbel-labu'.

The following botanical characteristics of the new and distinct variety of *Calibrachoa* plant named 'Sunbel-labu' were observed for plants growing outdoors in 24 cm pots at an age of approximately 9 months in Yokaichi-shi, Shiga-ken. During the production period, the average day temperature is approximately 22° C., the average night temperature is approximately 12° C.

Plant:
- *Growth habit.*—Spreading.
- *Plant height.*—Approximately 14.3 cm.
- *Spreading area of plant.*—Approximately 45 cm.
- *Blooming period.*—April to late October in the southern Kanto area, Japan. The plant shape does not change throughout this period.

Stem:
- *Thickness.*—Approximately 1.4 mm.
- *Length.*—Approximately 20 cm.
- *Pubescence.*—Sparse.
- *Branching.*—Abundant branching, especially lateral branching.
- *Internode length.*—Approximately 0.7 cm.
- *Color.*—Young, near R.H.S. 144B, mature, near R.H.S. 200C.

Leaf:
- *Whole shape.*—Lanceolate. The shape of the apex is acute, and the shape of the base is attenuate.
- *Margin.*—Entire.
- *Length.*—Approximately 1.8 cm.
- *Width.*—Approximately 0.8 cm.
- *Color.*—Upper side color is near R.H.S. 146A (moderate olive green). Bottom side color is near R.H.S. 146B (moderate yellow green).
- *Thickness.*—Approximately 0.4 mm.
- *Pubescence.*—Sparse.

Flower:
- *Facing direction.*—Slanted upward.
- *Type.*—Single.
- *Shape.*—Funnel-shape, with five-fissured limb.
- *Shape of petal chip.*—Rounded.
- *Lobation.*—Shallow.
- *Waviness of petal.*—Weak.
- *Diameter.*—Approximately 2.5 cm.
- *Throat diameter.*—Approximately 9.0 mm.
- *Corolla tube diameter.(distal end).*—Approximately 3.5 mm.
- *Corolla tube length.*—Approximately 13.0 mm.
- *Color.*—Petal (upper and lower surface near R.H.S. 76A (light purple) with near R.H.S. 77A (deep reddish purple) midvein. Bottom color of the corolla throat; near R.H.S. 14B (vivid yellow). Outside color of the corolla tube; near R.H.S. 182C (dark pink).
- *Reproductive organs.*—1 normal pistil and 5 normal stamens. The stigma is club-shaped and near R.H.S.N144D (light yellow green) in coloration. The style is approximately 6 mm in length and near R.H.S. 145B (brillant yellow green) in coloration. The ovary is near R.H.S. N144D (light yellow green) in coloration. The stamens commonly are of variable length from approximately 4.6 to 6.6 mm. Pollen is formed in a quantity that is typical of a *Calibrachoa* plant and is near R.H.S. 15D (light yellow) in coloration.

*Fertility.*—Fertile, but self-incompatible.

*Peduncle.*—Approximately 0.6 mm in diameter and approximately 0.7 cm in length. The texture is smooth.

*Calyx.*—Narrow with 5 sepals fused at the base.

*Seeds.*—Scarce. Near R.H.S.N 186A (strong red) in coloration, approximately 0.6 mm in diameter, and generally round.

Physiological and ecological characteristics: High resistance to cold, heat, rain and disease, such as powdery mildew. The resistance to heat and rain is very strong.

Blooming: This new variety of *Calibrachoa* plant is most suitable for flower bedding and potting, particularly in hanging pots or planters. Pinching of old blossoms will enhance the formation of new blossoms.

It is claimed:

1. A new and distinct variety of *Calibrachoa* plant named 'Sunbel-labu', substantially as herein illustrated and described.

* * * * *